United States Patent [19]
Gelmont et al.

[11] Patent Number: 5,703,274
[45] Date of Patent: Dec. 30, 1997

[54] PROCESS FOR THE PREPARATION OF 5-HYDROXYISOPHTALIC ACIDS

[75] Inventors: Mark Gelmont, Nesher; Joseph Bercovici, Kiriat Bialik; Jakob Oren, Nesher, all of Israel

[73] Assignee: Bromine Compounds Ltd., Beer-Sheva, Israel

[21] Appl. No.: 621,533

[22] Filed: Mar. 26, 1996

[30] Foreign Application Priority Data

Mar. 27, 1995 [IL] Israel ............................ 113142

[51] Int. Cl.$^6$ ................................. C07C 213/00
[52] U.S. Cl. ................................. 562/475
[58] Field of Search ....................... 562/480, 475

[56] References Cited

U.S. PATENT DOCUMENTS

| | | | |
|---|---|---|---|
| 2,756,149 | 7/1956 | Saunders et al. | 95/8 |
| 3,285,706 | 11/1966 | Cake | 23/277 |
| 3,914,294 | 10/1975 | Bernstein et al. | 260/519 |

FOREIGN PATENT DOCUMENTS

| | | |
|---|---|---|
| 0 092 772 | 11/1983 | European Pat. Off. . |
| 0 185 130 | 6/1986 | European Pat. Off. . |
| 0 195 402 | 9/1986 | European Pat. Off. . |
| 647610 A1 | 4/1995 | European Pat. Off. . |
| 1 947 264 | 3/1970 | Germany . |
| 1 966 188 | 10/1971 | Germany . |
| 291 990 | 7/1991 | Germany . |
| 51-52142 | 5/1976 | Japan . |
| 51-108030 | 9/1976 | Japan . |
| 60-35332 | 2/1985 | Japan . |
| 07223999 A2 | 8/1995 | Japan . |
| 07259117 A2 | 10/1995 | Japan . |

OTHER PUBLICATIONS

Davies, et al., Drugs of the Future, vol. 15, No. 11, 1990, pp. 1074–1076.
Gensler, et al., "Synthesis of Chaminic Acid",*Journal of Organic. Chemistry*, vol. 38, No. 9, 1973, pp. 1726–1731.
Johns, et al., "Synthetic Experiments in the cycloHeptatrienone Series. Some Derivatives of 4–Hydroxytropone", *Journal of Chemical Society*, 1955, pp. 309–313.
Johns, et al., "Synthetic Experiments in the cycloHeptatrienone Series. Syntheses of Puberulic Acid and isoStipitatic Acid",*Journal of Chemical Society*, 1954, pp. 198–202.
Hwang, et al., "Synthesis of 3, 5–Di–sec–butylphenol", *Agricultural and Biological Chemistry*, vol. 35, 1971, pp. 1812–1813.
McGrath, "Bromination of isophthalic acid",*Research Disclosure*, Jun. 1976, pp. 51–52.
Suter, "Tetracovalent Sulfur Compounds",*The Organic Chemistry of Sulfur*,pp. 229, 332–333, 1955.
Schreder, *Monatshefte for Chemie*, 1, 1880, p. 437.
Iavarone, et al., *Gazzetta Chimica Italiana*, 101, 1971, pp. 748–763.

*Primary Examiner*—Samuel Barts
*Attorney, Agent, or Firm*—Merchant, Gould, Smith, Edell, Welter & Schmidt, P.A.

[57] ABSTRACT

A process for the preparation of 5-hydroxyisophthalic acid (5-HIPA) that comprises hydrolyzing a starting material chosen from among 5-bromoisophthalic acid (5-BIPA), mixtures of 5-BIPA and dibromoisophthalic acid isomers, and salts of thereof in an aqueous alkaline solution, in the presence of a catalytically effective amount of a copper compound catalyst and in a temperature range of between 100° and 270° C.

12 Claims, No Drawings

PROCESS FOR THE PREPARATION OF 5-HYDROXYISOPHTALIC ACIDS

FIELD OF THE INVENTION

The present invention relates to the preparation of 5-hydroxyisophthalic acid (hereinafter 5-HIPA) by the hydrolysis, in aqueous alkaline solutions, of 5-bromoisophthalic acid (hereinafter 5-BIPA), or a mixture of 5-BIPA and dibromoisomers.

BACKGROUND OF THE INVENTION

5-HIPA is used as a starting material for a variety of products such as drugs, agrochemicals and polymers [WP 195,402; DD 291990; EP 185130; U.S. Pat. No. 3,914,294; Davies et al., Drugs of the Future, 15, 1074–1076 (1990)].

Various methods for the preparation of 5-HIPA are described in the art. Methods which invoke sulfonation of isophthalic acid (IPA), followed by caustic fusion are disclosed by Leonnies, Chem. Her. 18,. 705 (1880); Heine, Chem. Ber. 18, 494 (1880); U.S. Pat. No. 2,756,149; U.S. Pat. No. 3,285,706: Gensler and Solomon, J. Org. Chem., 38, 1726–1731 (1973); JP 51052142; JP 60085332; EP 92772. Other methods, based on diazotion of 5-aminoisophthalic acid are disclosed by Beyer, J. Prakt. Chem.(2) 25, 505–515 (1882). JP 51108030 discloses processes through which the 5-HIPA is obtained via oxidation of substituted xylene. 5-HIPA may be also prepared by alkaline rearrangement of tropone-carboxylic acids (such as 6-methoxy-3-oxocyclohepta-1,4,6-trienecarboxylic acid or 6-bromo-8-methoxy-5-oxocyclohepta-1,3,6-trienecaboxylic acid) in the presence of aqueous KOH, as dscribed by Johns et al., J. Chem. Soc. 309–318 (1955) and Johns et al., J. Chem. Soc. 198–202 (1954). Other procedures for the preparation of 5-HIPA, described by Schreder, Monatsch. Chem 1, 437 (1880) and Leger, Hebd. Seanoes Acad. Sci., 154, 283 (1912), require a reaction between hydroxy-anthraquinones systems and KOH. The art discloses still further processes, as e.g. in DE 1966188, DE 1947264, Iavarone et al., Gazz. Chim. Ital. 101, 748–763 (1971) and Hwang and Matsui, Agric. Biol. Chem., 35 1812–1813 (1971).

Among the prior art processes, the one based on sulfonation and caustic fusion appears to be the most effective. An example of the caustic fusion reaction is given in JP 51052142: caustic alkali is added to tri-Na-5-sulfoisophthalate containing 10% $H_2O$ at 250°, at a rate sufficient to keep the fusion mixture powdery throughout the treatment. The mixture is then maintained for 2 hours at 800°. Finally, the powdery product is dissolved in $H_2O$ and neutralized with HCl to give 90% 5-HIPA. Still, even this process is not fully satisfactory. The main shortcoming of this process is the use of a high reaction temperature together with a strong basic medium. Such "hard" reaction conditions lead to corrosion of the equipment used and necessitate its frequent replacement.

It is an object of the present invention to provide a simple and economic process for the preparation of 5-HIPA.

It is another object of the present invention to provide a process in which 5-HIPA is obtained in high yield and with high purity.

It is a further object of the present invention to provide a process which can be carried out under relatively mild temperature conditions.

Other objects and advantages of the present invention will appear as the description proceeds.

SUMMARY OF THE INVENTION

According to the invention, 5-HIPA is prepared by a process that comprises hydrolyzing 5-bromoisophthalic acid (5-BIPA) or a salt thereof or a mixture of 5-BIPA and dibromoisophthalic acid isomers or salts thereof, in the presence of a copper compound catalyst in an aqueous alkaline solution at a temperature between 100° and 270° C.

DETAILED DESCRIPTION OF PREFERRED EMBODIMENTS

5-BIPA can be produced in an economical manner by the bromination of isophthalic acid (IPA) (H. McGrath (1976), Res. Discl. 146, 51–52 (CA 85:123510d)) and can be hydrolyzed in the presence of a suitable catalyst and base at the relatively low temperature whereby to avoid the decarboxylation side reaction. The respective salts, e.g. monoalkali and/or dialkaliisophthalates, are equally suitable for the process, provided that the molar ratio of base to halogen atom equivalents, hereinafter specified, is maintained.

Another advantage of the present invention is that 5-HIPA of high purity (>97%) can be obtained from 5-BIPA containing dibromoisophthalic acid, which is produced in the bromination of isophthalic add (IPA), generally in amounts varying from about 2% to 20%. The hydrolysis temperature in this case, however, has to be high enough (>140° C.) so decompose the dihydroxyisophthalic acids (DHIPA) which we formed from the corresponding dibromo isomers.

The prior art discloses caustic fusion processes which occur readily at high temperatures, usually about 300° C. Lower temperatures were considered impractical because of the low hydrolysis rate, hence the advantage of operating at relatively low pressures associated with low reaction temperatures, could not be exploited. In the process of the invention this limitation has been removed, and the process may be conducted at temperatures lower than 180° C., preferably at 140°–200° C., under autogenous pressure.

The copper compound catalyst preferred is a catalyst of the formula $Cu(n)R(m)$, in which:

R is —O, —OH or the anion of an inorganic or organic acid;
n is 1 or 2; and
m is 0, 1 or 2.

Examples of copper compound catalysts of the invention are Cu, CuCl, CuO, $CuBr_2$, $CUCl_2$, CuBr, $Cu_2O$, $On(OH)_2$, $CuSO_4$, $Cu(OAc)_2$ and other known copper salts of organic and inorganic acids. One such copper compound catalyst can be used in the reaction, or mixtures of two or more of these compounds can be employed together. The total amount of copper compound catalysts in the reaction is between 1 to 5% by mole with respect to the starting material.

At the end of the hydrolysis step, the copper compound catalyst can be filtered off and reused in a subsequent reaction.

As stated hereinbefore, the hydrolysis of 5-BIPA or its salts or the mixtures thereof with dibromoisophthalic acid isomers or their salts is carried out in an alkaline aqueous solution. The alkali of said solution can be selected from the hydroxides, oxides and carbonates of sodium and potassium and mixtures thereof. The corresponding compounds of alkaline earth metals can also be used. The content of the alkali in the aqueous solution is between 4 and 10 times the equivalents of the halogen atom in the starting material, preferably between 5–7, calculated on a mole basis.

All the above and other characteristics and advantages of the invention will be better understood through the following illustrative and non-limitative examples of preferred embodiments.

EXAMPLE 1

A mixture of 5-BIPA (196 g, 0.8 moles), NaOH (160 g), $H_2O$ (640 g) and $Cu_2O$ (3.9 g, 0.027 moles) was placed into a one liter autoclave. The autoclave was sealed and heated to 140° C. Full conversion was achieved after 90 min. The autoclave was cooled to room temperature, opened, and the reaction mixture was filtered to remove the catalyst.

The filtrate was placed into a four-necked flask equipped with a stirrer, a condenser, a dropping funnel and a the thermometer and acidified to pH 1 with 82% HCl (350 ml) at 60°–80° C. until full dissolution was obtained. The mixture was then cooled by stirring, filtered and washed with water. After drying 138.3 g of a cream-colored solid, with a purity of 98.2%, was obtained (98.2% yield).

EXAMPLE 2

Example 1 was repeated, but instead of pure 5-BIPA, a mixture of 5-BIPA (91.5%) and dibromoisophthalic acid (8.3%) was used, and the autoclave was heated to 170° C. instead of 140° C. 5-HIPA (119.1 g) was obtained in a yield of 92.1% based on 5-BIPA, with a purity of 97.1%.

EXAMPLES 3–8

Examples 3–8 illustrate the effect of temperature on the hydrolysis of a mixture of 5-BIPA (91.5%) and dibromoisophthalic acid (8.3%) in the presence of a copper catalyst, at constant base to 5-BIPA ratio of 5:1. Example 2 was repeated under various conditions (see Table 1).

TABLE I

| Exam No. | Temp. °C. | Time hrs. | Conversion (% Br⁻) | 5-BIPA (%) | 5-HIPA % | DHIPA % | IPA % |
|---|---|---|---|---|---|---|---|
| 3 | 120 | 3 | 96 | 3.8 | 93.0 | 2.8 | 0.6 |
| 4 | 140 | 1.5 | >99 | N.D. | 96.3 | 3.1 | 0.7 |
| 5 | 160 | 1.5 | >98 | N.D. | 96.6 | 1.1 | 0.7 |
| 2 | 170 | 1.5 | >97 | N.D. | 97.1 | 0.7 | 0.8 |
| 6 | 190 | 1.0 | >97 | N.D. | 95.2 | 0.2 | 0.9 |
| 7 | 210 | 1.0 | >99 | N.D. | 98.0 | — | 0.8 |
| 8 | 250 | 1.0 | >99 | N.D. | 98.9 | — | 0.8 |

% = molar percent
5-BIPA = 5 bromoisophthalic acid
5-HIPA = 5 hydroxyisophthalic acid
DHIPA = dihydroxyisophthalic acid
IPA = isophthalic acid

EXAMPLES 9–11

Examples 9–11 illustrate the effect of changing the ratio of base to 5-BIPA (91.5%)/dihromoisophthalic acid (8.3%) mixture at constant temperature and catalyst concentration. Example 2 was repeated using various amounts of base as detailed in Table II.

TABLE II

| Example No. | Molar ratio NaOH/ 5-BIPA mixture | Conversion % Br⁻ | 5-BIPA % | 5-HIPA % | DHIPA % | IPA % |
|---|---|---|---|---|---|---|
| 9 | 3 | 95 | 4.2 | 83.5 | 6.8 | 3.8 |
| 10 | 4 | 96 | N.D. | 96.7 | 1.2 | 0.9 |
| 2 | 5 | 99 | N.D. | 97.1 | 0.7 | 0.8 |
| 11 | 6 | 99 | N.D. | 98.2 | 0.4 | 0.8 |

EXAMPLES 12–13

Examples 12–13 illustrate the effect of using different mounts of $Cu_2O$ catalyst on the hydrolysis of a mixture of 5-BIPA (91.5%) and dibromoisophthalic acid (8.3%). The experiment described in Example 2 was repeated. The modifications are detailed in Table III.

TABLE III

| Example No. | Reagent 5-BIPA (moles) | Reagent NaOH (moles) | Catalyst $Cu_2O$ (moles) | Temp. °C. | Time hrs. | Conversion % Br⁻ |
|---|---|---|---|---|---|---|
| 12 | 0.8 | 4.0 | 0.0001 | 170 | 1.5 | 85 |
| 13 | 0.8 | 4.0 | 0.001 | 170 | 1.0 | 96 |
| 2 | 0.8 | 4.0 | 0.027 | 170 | 1.0 | >99 |

All the above descriptions and examples have been given for the purpose of illustration and are not intended to constitute a limitation of the invention.

Many variations can be effected in the process of the invention. For instance, different alkalis may be used, different reagent ratios, reaction temperatures and catalysts can be employed, all without departing from the spirit of the invention of exceeding the scope of the claims.

We claim:

1. A process for the preparation of 5-hydroxyisephthalic acid (5-HIPA) that comprises hydrolyzing a starting material chosen from among 5-bromoisophthalic acid (5-BIPA), mixtures of 5-BIPA and dibromoisophthalic acid isomers, and salts of thereof in an aqueous alkaline solution, in the presence of a catalytically effective amount of a copper compound catalyst and in a temperature range of between 100° and 270° C.

2. A process according to claim 1, wherein the hydrolysis is carried out under autogenous pressure.

3. A process according to claim 1, wherein the alkali in the aqueous solution is selected from among the hydroxides, oxides and carbonates of sodium and potassium or mixtures thereof.

4. A process according to claim 1, in which the alkalis of the aqueous solution are used in an amount of more than 4 equivalents of the halogen atom in the starting material.

5. A process according to claim 1, wherein the catalyst comprises one or more compounds of the formula:

Cu(n)R(m), in which:

R is —O, —OH or the anion of an inorganic or organic acid;

n is 1 or 2; and m is 0, 1 or 2.

6. A process according to claim 1, in which copper compound catalysts may be used either individually or in mixtures in an amount of between 0.1–20% by mole.

7. A process according to claim 5, wherein the catalyst is chosen from among Cu, CuCl, $CuCl_2$, $CuBr_2$, $Cu_2O$, $Cu(OH)_2$, $CuSO_4$, and $Cu(OAc)_2$.

8. A process according to claim 1, wherein the temperature range is 100°–270° C.

9. A process according to claim 1, comprising preparing the 5-BIPA by bromination of isophthalic acid (IPA).

10. A process according to claim 1, wherein the salts are alkali salts.

11. A process according to claim 6, in which copper compound catalysts may be used either individually or in mixtures in an amount of between 1.0–5.0% by mole.

12. A process according to claim 8, wherein the temperature range is 140°–200° C.

* * * * *